(12) United States Patent
Nandigala et al.

(10) Patent No.: US 10,946,141 B2
(45) Date of Patent: Mar. 16, 2021

(54) STERILE PROTECTIVE COVER COMPRISING A DEVICE FOR OPTHALMIC DELIVERY

(71) Applicants: Virchow Biotech Pvt. Ltd., Hyderabad (IN); Virchow Biotech Inc., Arlington, VA (US)

(72) Inventors: Hemanth Nandigala, Hyderabad (IN); Murali Krishna Reddi Tummuru, Hyderabad (IN); Prasad Vure, Hyderabad (IN)

(73) Assignees: Virchow Biotech Pvt. Ltd., Hyderabad (IN); Virchow Biotech Inc., Arlington, VA (US)

( * ) Notice: Subject to any disclaimer, the term of this patent is extended or adjusted under 35 U.S.C. 154(b) by 0 days.

(21) Appl. No.: 15/876,832

(22) Filed: Jan. 22, 2018

(65) Prior Publication Data
US 2018/0140461 A1    May 24, 2018

Related U.S. Application Data

(63) Continuation-in-part of application No. 15/724,673, filed on Oct. 4, 2017, now abandoned, which is a
(Continued)

(30) Foreign Application Priority Data

Mar. 14, 2016 (IN) .............................. 201641008743
Aug. 11, 2017 (IN) .............................. 201743028628
Oct. 28, 2017 (IN) .............................. 201743038325

(51) Int. Cl.
*A61M 5/178* (2006.01)
*A61M 5/24* (2006.01)
(Continued)

(52) U.S. Cl.
CPC ......... *A61M 5/2466* (2013.01); *A61F 9/0008* (2013.01); *A61M 5/24* (2013.01);
(Continued)

(58) Field of Classification Search
CPC ... A61M 5/3202; A61M 5/31546; A61M 5/34
See application file for complete search history.

(56) References Cited

U.S. PATENT DOCUMENTS 4,757,381 A * 7/1988 Cooper .............. A61B 1/00091
  206/369
5,328,481 A * 7/1994 Wang ................. A61F 9/00736
  604/143
(Continued)

*Primary Examiner* — William R Carpenter
(74) *Attorney, Agent, or Firm* — Pitch, Even, Tabin & Flannery LLP

(57) ABSTRACT

Described herein does a sterile protective cover comprise an intracameral therapeutic agent delivery device in the form of a pen-injector comprising a cartridge container for dispensing multiple doses of a medicament, coupled to an actuation assembly within a housing. A needle assembly is coupled to the distal end of the cartridge container, provided with a removable cap received within the housing will be in optional pre-sterile or no-sterile condition. Use of such device for the prevention or treatment of ocular conditions or diseases is also disclosed. A sterile protective cover comprising ophthalmic device, wherein the sterile protective cover is made of plastic, polythene, polyethylene, resin, rubber, polystyrene, polypropylene, polycarbonate, nylon, or combination thereof. More, particularly the present invention relates to a novel ophthalmic device of reduced length and diameter in the form of a pen-injector for precise and controlled delivery of different doses of a therapeutic agent by introducing a unique "Pen grip" for the device. The present invention also depicts a novel ophthalmic device comprising a multimode power on-off button that would also work with a "Pulse mode" to deliver a fixed quantity of
(Continued)

medicament and also double up as a speed control to control the rate of injection and might be used with dermal filler.

16 Claims, 12 Drawing Sheets

Related U.S. Application Data continuation-in-part of application No. 15/455,892, filed on Mar. 10, 2017, now abandoned.

(51) Int. Cl.
    *A61F 9/00*     (2006.01)
    *A61M 5/315*     (2006.01)
    *A61M 5/28*     (2006.01)
    *A61M 5/20*     (2006.01)

(52) U.S. Cl.
    CPC ............ *A61M 5/2455* (2013.01); *A61M 5/28* (2013.01); *A61M 5/288* (2013.01); *A61M 5/31546* (2013.01); *A61M 5/20* (2013.01); *A61M 5/281* (2013.01); *A61M 2005/2403* (2013.01); *A61M 2005/244* (2013.01); *A61M 2005/2411* (2013.01)

(56) References Cited

U.S. PATENT DOCUMENTS

| | | | | |
|---|---|---|---|---|
| 5,332,092 | A * | 7/1994 | Fischer | A61M 5/002 206/305 |
| 6,652,489 | B2 * | 11/2003 | Trocki | A61M 5/14546 604/154 |
| 7,748,980 | B2 * | 7/2010 | Mulhauser | A61C 5/64 222/137 |
| 2007/0270744 | A1 * | 11/2007 | Dacquay | A61F 9/0017 604/114 |
| 2007/0270750 | A1 * | 11/2007 | Dacquay | A61F 9/0017 604/151 |
| 2010/0145305 | A1 * | 6/2010 | Alon | A61M 5/20 604/506 |
| 2014/0079686 | A1 * | 3/2014 | Barman | A61K 8/69 424/94.67 |
| 2014/0142507 | A1 * | 5/2014 | Armes | A61M 5/20 604/112 |
| 2015/0328405 | A1 * | 11/2015 | Metzner | A61M 5/20 604/143 |
| 2016/0270893 | A1 * | 9/2016 | Tapocik | A61C 19/066 |
| 2018/0133400 | A1 * | 5/2018 | Almoumen | A61M 5/3137 |

* cited by examiner

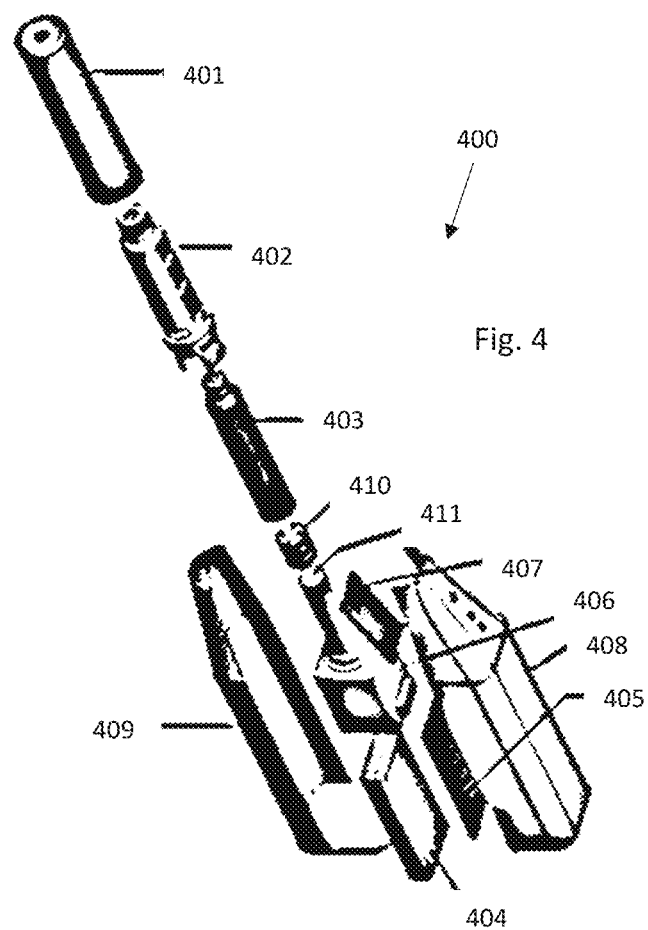

STERILE PROTECTIVE COVER COMPRISING A DEVICE FOR OPTHALMIC DELIVERY

CROSS-REFERENCE TO RELATED APPLICATION

This application is a continuation-in-part of application Ser. No. 15/724,673 filed on 4 Oct. 2017, which is a continuation-in-part of U.S. patent application Ser. No. 15/455,892, filed on Mar. 10, 2017, and further claims the benefit of Indian Patent Application Number 201743028628, filed on 11 Aug. 2017, Indian Patent Application Number 201743038325, filed on 28 Oct. 2017, and Indian Provisional Application Number IN 201641008743, filed on Mar. 14, 2016, all of which are incorporated herein by reference in their entirety.

FIELD OF INVENTION

The present invention relates to a novel ophthalmic delivery device for dispensing a therapeutic agent into ocular tissues of the patients in need thereof. More, particularly the present invention relates to a novel ophthalmic device of reduced length and diameter in the form of a pen-injector for precise and controlled delivery of different doses of a therapeutic agent.

BACKGROUND

Ophthalmic drug delivery is one of the most interesting and challenging endeavors facing the pharmaceutical scientist. The landscape of ophthalmic drug delivery is highly competitive and rapidly evolving. New classes of pharmaceuticals and biologics are fueling the demand for novel drug delivery. The main aim of pharmacotherapeutics is the attainment of effective drug concentration at the site of action for sufficient period of time to elicit a response. The challenge is to provide a system with improved ocular drug bioavailability and prolonged duration of activity, but still with a minimum risk of ocular complications. A major problem of ophthalmic drug delivery is not the lack of efficient drugs but the attainment of their optimal, precise and controlled concentration at the site of their action. Most of the formulation efforts aim at maximizing ocular drug absorption through prolongation of the drug residence time in the cornea and conjunctival sac, as well as to slow drug release from the delivery system and minimize corneal drug loss. The emergence of new and innovative means for improving therapeutic efficacy suggests that a greater choice of delivery systems will be provided to physicians and patients in the next decade.

The eye is a complex organ with a unique anatomy and physiology. The structure of the eye can be divided into two main parts: anterior segment and posterior segment. Tissues such as conjunctiva, cornea, iris, ciliary body, lens and aqueous humor make up the anterior segment. Posterior segment of the eye includes sclera, choroid, retina, vitreous humor and optic nerve. Diseases affecting the anterior segment of the eye include cataract, glaucoma, anterior uveitis, allergic conjunctivitis while the posterior segment of eye is mostly affected by age-related macular degeneration, diabetic nephropathy and other retina related diseases.

Historically, the treatment of ocular diseases or conditions has been effected through the use of ophthalmic drugs in the form of eye drops, being the most convenient route of administration. However, this means of ophthalmic drug delivery has numerous problems. Delivery of drugs to targeted ocular tissues is restricted by various corneal, both dynamic and static, ocular barriers. Also, therapeutic drug levels are not maintained for longer duration in target tissues. For example, an average eye drop far exceeds the normal eye's capacity, effectively destabilizing and stripping the natural tear film. This causes a brief period of massive over dosage which is quickly cleared by lacrimation, blinking and nasolacrimal drainage resulting in sub-therapeutic drug levels until next application, showing inefficient pharmacokinetics. Further, regular use of eye drops often result in local irritation and toxicities.

As such the delivery of drugs or bioactive agents to different regions of the eye, such as the retina, vitreous, anterior chamber, and uveal tract is typically achieved by high systemic dosing, intra-ocular injections or other measures. Penetration of systemically administered drugs into the retina or other portions of the eye is severely restricted by the blood-retinal barrier (BRB) for most compounds. Although intravitreal injections, resolves some constraints posed by the BRB and significantly reduces the risk of systemic toxicity, such techniques may result in retinal detachment, physical damage to the lens, exogenous endophthalmitis, and also may result in high pulsed concentrations of therapeutic agent at the lens and other intraocular tissues.

Even further, treatment of ocular conditions such as glaucoma and cataract are very challenging. Approaches have been made to overcome the ocular drug delivery barriers and improve the ocular bioavailability by the use of novel drug delivery systems such as emulsions, particulate suspensions, ointments, aqueous gels, nanoparticles, liposomes, nanomicelles, dendrimers, implants, contact lenses, nanosuspensions, and micro needles.

Further, surgical techniques for cataract have undergone remarkable development and improved over time requiring less anesthesia and decreased need for hospitalization. However, surgical procedures for cataract extraction involving the use of conventional intraocular injections may be associated with serious complications such as accidental injection into the retina, choroid vasculature, or intravitreal space resulting in perforation of the globe. The effects associated with the perforation of the globe include pain, reduced vision, ocular hypertension or intraocular hemorrhage.

However, the ophthalmic literature is rife with references to the need for a better means of ophthalmic drug delivery. The present inventors intend to provide novel drug delivery devices, particularly for administration of therapeutic agents to anterior chamber or posterior chambers of the eye.

Currently, injections for intracameral delivery are available in the market in the form of single dose prefilled syringes for the treatment of ocular conditions associated with anterior chamber of eye such as cataract, glaucoma. However, such devices are not precise or controlled in their delivery mechanism. Also, there is no feedback as the regards the quantity of drug used.

The major drawbacks associated with the existing ophthalmic delivery devices are that they are not integrated systems and are manually operated. The other challenges posed by the convention prefilled syringes are that a high level of manual control has to be guaranteed to place the medicament in the target area. Therefore, it is particularly disadvantageous because manual dexterity decreased when high forces have to be exerted. A precise control on extrusion force for dispensing the medicament is needed, failing which leads to burst release and loss of the medicament.

Hence, it lacks precision and control in dispensing a predetermined dose of a medicament.

Improperly sealed prefilled syringes also result in loss of medicament. Also, the conventional syringes are not designed to dispense medicaments of varying viscosities.

There is no such device available in the market for administration of medicament into the eye, or in any form in public domain.

Again, postoperative infection is the most dreaded complication in the ophthalmology. Prevention is the responsibility of the operating surgeon. Asepsis and antisepsis is a science and as similar to cataract surgery, it has also made rapid advances recently. The incidence of infection in the western world has gone down to 1:10,000 or 15,000. In case of India the statistics is approximately 1:1000. Infection is caused by the organisms entering the eye during surgery. No matter, how vigilant we are, a few organisms will gain entry into the eye. And there is a strong source of these infections that is surgical instruments and devices. So sterilizing those devices prior to the surgery is mandatory.

The instruments are brought in direct contact with the patient's eye. In order to prevent transfer of infections from patient to patient, such optical instruments, especially the eye-contacting portions thereof, must be properly sterilized before use. The sterilization procedure most widely used in practice is treatment in an autoclave and Gas sterilization exclusively for heat sensitive materials. The marketed devices are packed within the non-sterile packages so the user has to sterilize the product before using, thus increasing the inconvenience of the health care providers.

Again, there has been a constant need amongst the cosmetologists regarding the control of the device specifically while injecting on the face.

Moreover, there exists a need to develop novel drug delivery devices for effectively treating ocular diseases and conditions, with few or no negative side effects.

OBJECTS OF THE INVENTION

It is an object of this invention to provide a novel ophthalmic device for the delivery of medicament into the anterior chamber of eye.

It is also an object of the invention to provide an intracameral and/or ophthalmic device in the form of a pen for the delivery of precise doses of a medicament.

Another object of the invention is to overcome the above-mentioned difficulties and shortcomings of the already existing ophthalmic drug delivery systems.

It is an object of the invention to provide an intracameral delivery device in the form of a pen injector which comprises a housing comprising a sterile, cartridge container containing a cartridge comprising doses of medicament confined by a piston at its proximal end; a needle assembly at its distal end for dispensing the medicament with a removable cap or a needle cover; coupled to an actuation assembly at the proximal end.

It is also an object of the invention to provide an ophthalmic delivery device in the form of a pen injector which comprises an over cap at the distal end of the device provided with a housing for covering a sterile, cartridge holder containing a cartridge comprising doses of medicament, confined by a piston at its proximal end; said over cap affixed onto an actuation assembly consisting an arrangement of a motor driven by a battery, supported by one or more printed circuit boards (PCB), said actuation assembly on the proximal end of the device is covered by housing on the top and bottom, and is directed towards the piston by means of a plunger rod connected to the motor.

Yet another object of the invention is to provide a novel ophthalmic delivery device adapted for injecting predetermined doses of medicament into the anterior chamber of the eye such that, the said device provides flexibility to the operator, a precise control over it, especially during surgery not requiring the exertion of significant forces for application of an injection or not changing the standard technique of application.

Another object of the invention is to provide an ophthalmic device for intracameral delivery in the form of a pen injector, flexible for use with wide variety of therapeutic agents.

It is also an object of the invention to provide intracameral drug delivery device in the form of a pen-injector for the treatment of ocular diseases and conditions associated with anterior chamber of the eye.

It is also an object of the invention to provide balanced salt solution as supplement for the treatment of ocular diseases and or conditions associated with anterior chamber of the eye.

SUMMARY OF INVENTION

The present invention relates to a novel ophthalmic device in the form of a pen-injector for delivery of a therapeutic agent in to the anterior chamber of eye to a subject in need thereof. In some embodiments the ophthalmic device is of reduced length and diameter in the form of a pen-injector for precise and controlled delivery of different doses of a therapeutic agent by introducing a unique "Pen grip" for the device by adding the control buttons near to the tips instead of behind the cartridges. The inventors of the present invention modified the control of the device by introducing some alteration in the device grip so that inconvenience of prior art devices could be over thrown. The present Invention also relates to a disposable sterile protective cover on an ophthalmic delivery device that is in a form of a pen injector for dispensing a therapeutic agent into ocular tissues of the patients in need thereof. The use of such a disposable cover eliminates the sterilization process of device pre-administration. The present invention also depicts a novel ophthalmic device comprising a multimode power on-off button that would also work with a "Pulse mode" to deliver a fixed quantity of medicament and also double up as a speed control to control the rate of injection.

The present inventors have surprisingly found that improved treatment may be obtained by providing a novel ophthalmic device in the form of an auto injector that is electronically controlled for delivering precise doses of medicament for treatment/surgeries associated with ocular conditions of anterior chamber of eye. More particularly, the ophthalmic device of the present invention may be valuable in treatment of conditions/diseases of the eye or surgeries that require drugs to be administered under sterile conditions. In some forms, sterile disposable protective plastic covered drug delivery devices are provided for effectively treating ocular diseases and conditions, with few or no negative side effects. Present inventors amazingly came up with a solution for ensuring the sterility of the device by inserting the device in a plastic made cover and sterilizing the complete package instead of the device alone imparting it a cost effective, compliant to Health care Providers and, most importantly, beneficial to the patients.

In some embodiments, the present invention more particularly relates to a novel ophthalmic drug delivery device in the form of a cable-free motor controlled auto injector for ocular delivery of medicament for single dose or multiple dose or combinations thereof. In some embodiments, the present invention also relates to a sterile disposable protective plastic covered drug delivery ophthalmic device in the form of a cable-free motor controlled auto injector for ocular delivery of medicament for single dose or multiple dose or combinations thereof.

In one embodiment, the present invention provides a novel, electronically controlled intracameral pen injector for precise and controlled delivery of single doses of medicament for the treatment of ocular conditions or diseases.

In another embodiment, the present invention provides a novel, cable-free motor driven intracameral pen injector for precise and controlled delivery of multiple predetermined doses of medicament for the treatment of ocular conditions or diseases.

In a further embodiment, the present invention provides a novel, intracameral drug delivery device in the form of a pen injector which may be electronically controlled, or cable-free motor actuated, or software controlled or combinations thereof.

In an embodiment, the present invention provides a novel intracameral drug delivery device in the form of a pen injector, designed to improve the manual dexterity while performing the operation of the device.

According to an embodiment the pen injector of the present invention is constructed to comprise a unique, sterile cartridge for housing the medicament so as to maintain sterility, particularly during surgical procedures.

In another embodiment, the pen injector of the present invention comprises an over cap so designed to cover a cartridge holder for containing a sterile cartridge comprising the medicament so as to maintain sterility, particularly during surgical procedures.

In another embodiment, the intracameral pen-injector of present invention comprises an actuation assembly at the proximal end, driven by a cable-free electrically actuated motor by means of a printed circuit board, so constructed with wide range of viscosity handling characteristics.

In another embodiment, the housing of the intracameral pen-injector is adapted to comprise easy swappable housing covers to ensure the sterility within the housing.

In yet another embodiment, the novel intracameral pen-injector of the present invention is more economical to the manufacturer and consumer in that, the unnecessary parts of the previous drug delivery devices are removed, especially with regards to syringe assemblies thereby reducing the overall cost of medication and surgery.

In a further embodiment, the present invention provides a novel ophthalmic delivery device in the form of a pen injector for intracameral drug delivery, which is handy, mobile, easily rechargeable, flexibility to operate with or without a cable.

In one embodiment, the present invention provides an intracameral delivery device in the form of a pen-injector comprising a housing comprising; a cartridge container with a pre-sterile cartridge having an opening therein comprising the medicament, confined at the proximal end by a piston slidably received within the rearward opening of the cartridge; with a needle assembly at its distal end operative to dispense the medicament there through during the operation; a removable cap or a needle cover, covering the needle assembly partially received within the housing; an actuation assembly secured within the housing comprising a plunger rod, a compressible spring, a motor, and a rechargeable/replaceable battery that provides the electrical energy for driving the piston within the cartridge for dispensing the medicament by means of a spring securely placed between the cartridge assembly and the actuation assembly within the housing of the device.

In another embodiment, the present invention provides an intracameral delivery device in the form of a pen-injector comprising a cartridge assembly consisting of cartridge holder with a pre-sterile cartridge having an opening therein comprising the medicament, confined at the proximal end by a piston slidably received within the rearward opening of the cartridge; an actuation assembly secured within a housing comprising a plunger rod, a motor, a printed circuit board (PCB) with dose setting buttons on it and a rechargeable/replaceable battery supported by a PCB that provides the electrical energy for driving the motor and thereby the piston within the cartridge for dispensing the medicament by means of the plunger rod extending from the motor towards the piston of the cartridge within the housing of the device. The housing comprising the actuation assembly connected to the cartridge assembly is externally covered by an over cap. During operation, the over cap is removed and a needle assembly is fixed to the opening of the cartridge holder for delivering the medicament.

In preferred embodiments, the cartridge holder and a pre-sterile cartridge constitute a separate isolated unit, which may be easily attached during operation or detached when not in use. The isolated unit is so designed as to facilitate easy and firm locking of the said unit with the device at the time of dispensing the medication. The isolated unit may be sterilized and fixed to the device so that the medicament may be used during surgery or post-surgery as and when required.

In an embodiment, the present invention provides a novel ophthalmic drug delivery device in the form of a pen-injector for dispensing predetermined doses of a medicament. In the present context, the housing of the pen-injector is preferably cylindrical, oval or elliptical in shape, which is more ergonomic. Such design of the device prevents the injector from rolling off a table or a flat surface.

In another embodiment, the pen-injector for intracameral delivery provides a cartridge container disposed within the housing. The cartridge container comprises a cartridge comprising doses of medicament with an opening at its proximal end, medicament being confined by a piston. The cartridge container is constructed having a cylindrical housing at its proximal end so as to house the plunger rod of the actuation assembly. Further, the cartridge container is connected to a needle assembly at the distal end of the cartridge with an opening for dispensing the medication there through.

In some embodiments, the cartridge container is provided with an opening for facilitating the attachment of a needle during operation for dispensing the medication there through.

In an embodiment, the over cap is so designed that it is held in a locked position to prevent the cover from being retracted to expose the cartridge assembly.

In some embodiments, the pen-injector of the present invention comprises an actuation assembly comprising a plunger rod, a motor, a PCB with buttons for dosage adjustment, a rechargeable/replaceable battery supported by a PCB, wherein the battery provides power for activation of the actuation assembly. The motor is configured to drive the plunger rod through the cartridge by means a piston slidably received through the cartridge. The electrical power provided by the battery forms the driving force for ejection of a calculated dose of medicament from the cartridge through the needle. The injection device according to the present invention is also characterized by the fact that the motor may be cable-free and electrically actuated.

In another embodiment, the present invention provides an intracameral injection device such that the said device does not impose on an operator or a practitioner or the user, a requirement of exerting a significant amount of force for performing an injection. A simple touch/button based operation enables the user to deliver the precise and controlled quantity of the drug. Further, a cable-free electrical actuation of the motor provides better flexibility to the user while performing the injection.

In another embodiment, the present invention provides balanced salt solution as supplement for the treatment of ocular diseases and or conditions associated with anterior chamber of the eye.

One of the embodiments of the present invention relates with sterile protective cover on drug delivery devices.

One of the embodiment of the present invention describes the sterile protective cover is preferably made of plastic, more preferably made of thermoplastics, most preferably Polyethylene.

Another embodiment of the present invention portrays the advantages of using sterile covered device over non-sterile covered devices.

In some embodiments, an intracameral delivery device is provided in the form of a pen injector which comprises a housing comprising a sterile, cartridge container containing a cartridge comprising doses of medicament confined by a piston at its proximal end; a needle assembly at its distal end for dispensing the medicament with a removable cap or a needle cover; coupled to an actuation assembly at the proximal end.

In some embodiments, an ophthalmic delivery device in the form of a pen injector is provided which comprises an over cap at the distal end of the device provided with a housing for covering a sterile, cartridge holder containing a cartridge comprising doses of medicament, confined by a piston at its proximal end; said over cap affixed onto an actuation assembly consisting an arrangement of a motor driven by a battery, supported by one or more printed circuit boards (PCB), said actuation assembly on the proximal end of the device is covered by housing on the top and bottom, and is directed towards the piston by means of a plunger rod connected to the motor.

Some embodiments provide a novel ophthalmic delivery device adapted for injecting predetermined doses of medicament into the anterior chamber of the eye such that, the said device provides flexibility to the operator, a precise control over it, especially during surgery not requiring the exertion of significant forces for application of an injection or not changing the standard technique of application.

In some embodiments an intracameral injection device is provided in the form of a pen-injector, adapted for use with container variations.

In some embodiments an ophthalmic device for intracameral delivery is provided in the form of a pen injector, flexible for use with wide variety of therapeutic agents.

In some embodiments an intracameral drug delivery device is provided in the form of a pen-injector for the treatment of ocular diseases and conditions associated with anterior chamber of the eye.

In some embodiments a balanced salt solution is provided as a supplement for the treatment of ocular diseases and or conditions associated with anterior chamber of the eye.

In some embodiments a sterile disposable protective plastic cover is provided over the said drug delivery ophthalmic device to avoid sterilization step before administration.

In some embodiments a sterile disposable protective plastic cover is provided over the said ophthalmic device to ensure the user compliance and patient benefits.

Another unique embodiment of the present invention provides an intracameral injection device in the form of a pen-injector, adapted for use with container variations being shorter in length and thinner in periphery than devices described in the prior arts.

Some embodiments provide an ophthalmic device of short length and narrow perimeter and enabled of a better grip by keeping the control buttons near the tip of the device, preferably 'Pen grip' to achieve a good control over the device. In some embodiments, an ophthalmic auto injector device with a multi-mode power on-off button is provided that would also work with a pulse mode to deliver a fixed quantity of product and also double up as a speed control to control the rate of injection thus imparting the user compliance and patient benefit. In some embodiments an ophthalmic device contains an OLED Screen to provide a visual indicator of the quantity of medicament injected and/or quantity of medicament left inside the device after the medication is injected.

One of the embodiments of present invention relates to the unique feature of the device that extends the usage of the said device even with the dermal filler.

BRIEF DESCRIPTION OF THE DRAWINGS

FIG. 1b describes the housing assembly of the device shown in FIG. 1a.

FIG. 4 is a representation of the exploded view of the delivery device.

FIG. 9(a-c) also demonstrates the Pen like grip of the device instead of a 'chop stick grip.'

DETAILED DESCRIPTION

Figure 1A:
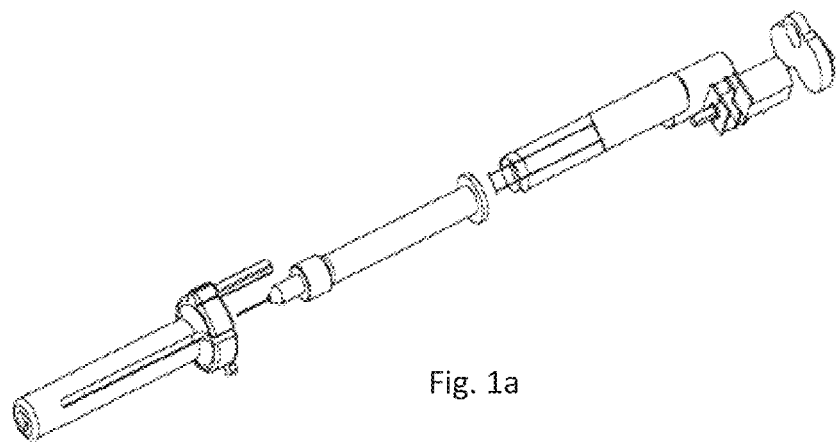
FIG. 1a is a perspective view of an injection device in accordance with one aspect of the invention.

The present invention provides novel ophthalmic devices for intracameral delivery of therapeutic agents in the form a pen-injector for the treatment of ocular diseases and conditions in subject in need thereof. The present invention also provides a sterile plastic protective cover on a novel ophthalmic device for intracameral delivery of therapeutic agents in the form a pen-injector for the treatment of ocular diseases and conditions in subject in need thereof.

It is to be understood that the terminology used herein is for the purpose of describing particular embodiments of the invention and is not intended to be limiting.

Unless otherwise defined, all technical and scientific terms used herein have the same meaning as commonly understood by one having ordinary skill in the art to which the invention pertains.

As used herein, the term "ocular" or "ophthalmic" refers to any area of an eyeball including without limitation, the anterior chamber, the posterior chamber, the vitreous cavity, the choroid, the suprachoroidal space, the conjunctiva, the subconjunctival space, the episcleral space, the intracorneal space, the epicorneal space, the sclera, the pars plana, surgically-induced avascular regions, the macula, and the retina.

The term "ocular condition" as used herein refers to a disease, ailment or a condition which affects or involves the eye or one of the parts or regions of the eye. Particularly, the present invention provides a pen type auto injector for the treatment of ocular conditions associated with anterior chamber of the eye.

As used herein the term "anterior ocular condition" refers to a disease, ailment or a condition which affects or involves an anterior ocular region or site, such as a cataract of the lens, or an ailment of the periocular muscle, an eye lid or an eye ball tissue or fluid which is located anterior to the posterior wall of the lens capsule or ciliary muscles.

The terms "medicament", "therapeutic agent", "active agent", "drug" used interchangeably herein refer to and include, an agent, drug, compound, composition of matter, or mixture thereof, including its formulation, which provides some beneficial effect.

It is to be understood that more than one agent can be combined or mixed together and incorporated into or used by the present invention, and that the use of the terms "medicament", "therapeutic agent", "active agent" in no way excludes the use of two or more such "medicaments", "therapeutic agents", "active agents".

The term "intracameral delivery" as used herein refers to the delivery of medicament in to the anterior chamber of the eye.

As used herein, the term "distal" shall designate the end or direction of the injection. The term "proximal" shall designate the end or direction towards the rear of the injection. The term "Sterile" signifies absence of any microorganisms. Sterilization is the process of killing all microorganisms (bacterial, viral, and fungal) with the use of either physical or chemical agents.

Classical sterilization techniques using saturated steam under pressure or hot air are the most reliable and should be used whenever possible. Other sterilization methods include filtration, ionizing radiation (gamma and electron-beam radiation), and gas (ethylene oxide, formaldehyde).

The term "Plastic" signifies material consisting of any of a wide range of synthetic or semi-synthetic organic compounds that are malleable and so can be molded into solid objects. It falls under a wide range of polymers like Polyamides or nylons, Polycarbonates, Polyesters, Polyethylene, Poly vinyl chloride, Poly vinylidene chloride, Acrylonitrile butadiene styrene or combinations thereof.

The intracameral delivery device of the present invention is a pen-injector comprising a housing for a pre-sterile cartridge container and an actuation assembly secured together within the housing by a locking system.

In some embodiments, the body of the housing is preferably cylindrical, oval or elliptical in shape, such that it is ergonomic. Such design prevents the device from rolling off a table or a flat surface, while providing a greater surface area for printing user instructions. The outer body of the housing is preferably formed from a synthetic material such that it can be easily molded. The outer body of the housing may be transparent so as to easily view the inner components through the outer body. It is also contemplated that the outer body may be opaque such that the interior components are not visible through the outer body. It is also contemplated that a label may be affixed to the outer body, which may increase the rigidity of the outer body.

In preferred embodiments, the device comprises a cartridge holder made of polypropylene disposed within the housing.

In another embodiment, the whole assembly comprising the cartridge within the housing may be sterile or optionally nonsterile.

In the present context, a pre-sterile cartridge is received within the cartridge holder comprising single or multiple doses of a medicament, having an opening at the proximal end for receiving the injection material, rearwardly confined by a piston made of polypropylene to be acted upon by a plunger rod by means of a motor driven force of the device. The cartridge container has a closed front end having an opening therein sized to receive only the needle there through during a medicament dispensing operation and a circumferential flange at the rear adaptable for engaging with the actuation assembly within the housing.

FIG. 1a represents a perspective view of one example of a drug delivery device according to the present invention. In the embodiment shown in FIG. 1b, an actuation assembly (110) within a housing has a proximal end and distal end. The actuator shown has an outer body (111). The distal end portion of the actuation assembly may have a coupler (112) with two hinges (113) that are disposed approximately equidistance circumferentially about the coupler (112), configured to engage the flange of the cartridge container (115) of the cartridge (114) at two distinct circumferential locations where the coupler (112) is hinged to the cartridge container. In the embodiment shown in FIG. 1b, a piston (120) is provided at the proximal end (121) of the cartridge (114). Positioned at the distal end (122) of the cartridge is a regulator (123), coupler (124), hub (125), and needle or other applicator (126).

Figure 2:
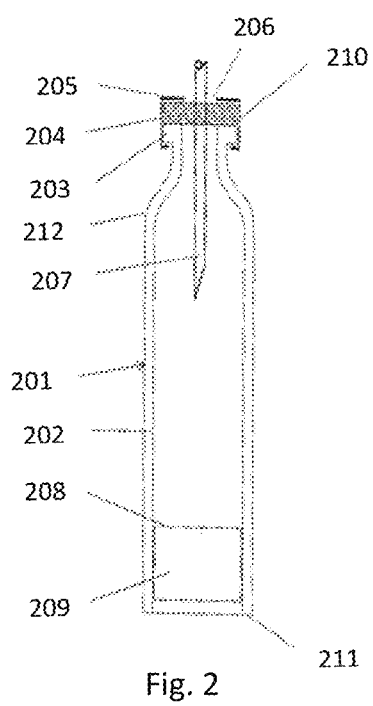
FIG. 2 illustrates a cartridge assembly.

The cartridge of the present invention may be well described with reference to FIG. 2, wherein the cartridge (201) comprising a cylindrical wall (202) has a distal end (210), which terminates in a neck part ending in circumferential flange (203) against which a piercable and flexible membrane (204) is held sealingly by a cap (205). At a central part of the membrane (204) the cap (205) has an opening (206) through which the membrane (204) is exposed. A hollow conduit (207), such as an injection needle can be stuck through the membrane (204) to communicate with the inner space of the cartridge (201) in which the medicament is stored between the membrane (204) and a front wall (28) of a piston (209) which fits into the cartridge (201). The piston (209) is usually made from a suitable material, such that it is tightly sealed against the inside of the cylindrical wall (202).

In another embodiment, the cartridge is adapted to be attached to a needle assembly at its distal end to dispense the medicament therethrough during operation. The cartridge housing may be sterile or non-sterile, further attached to routine plunger rods, further with motor driven electrically from a rechargeable/replaceable battery. In preferred embodiments, the needle assembly may comprise bent or straight needles of various lengths and sized customized for delivering the medicament into the eye.

In yet another embodiment, the ophthalmic delivery device of the present invention may further comprise a removable cap or a needle cover covering the needle assembly, received within the housing. The needle cover is so designed that it is held in a locked position to prevent the cover from being retracted to expose the needle. The removable cap or needle cover can be replaced by the user during operation of the device. Preferably, the outer dimensions of the needle cover are similar or identical to the dimensions of the outer body of the housing. Such construction provides an impression of a unitary whole when the removable cap is in position covering the needle assembly.

Figure 3:
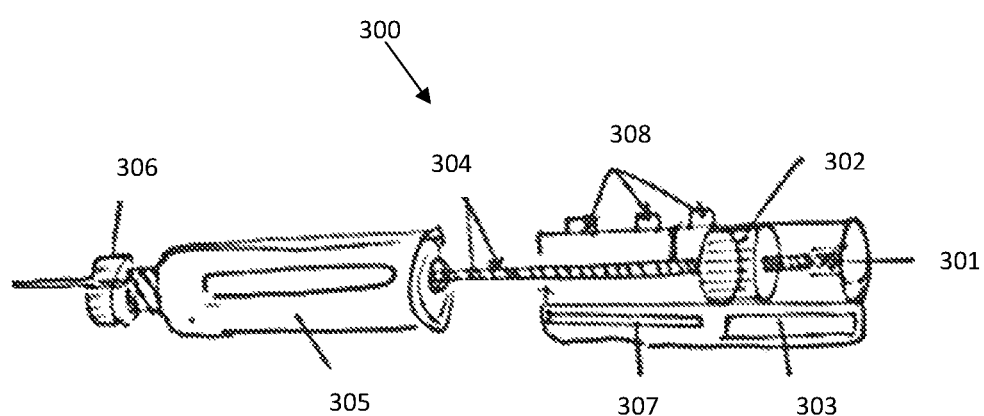
FIG. 3 illustrates the overall assembly of a delivery device.

In some embodiments the invention provides an intracameral delivery device in the form of a pen-injector (300) comprising a spring (301) of compressed or open type which drives the motor (302). The actuation assembly comprises a rechargeable/replaceable battery (303), connected to a motor and a compressible spring. The actuation assembly further comprises a movable plunger rod (304) adjacent to the proximal end portion of the cartridge container. The actuation assembly is configured within the housing (305) such that it is extendable in a distal direction to cause the extrusion of the injectable medicament from the cartridge through a needle (306) or other applicator when the cartridge is coupled to the actuation assembly. The device may also contain a printed circuit board (307) coupled to the motor and to buttons (308) for delivering accurate doses of a medicament. FIG. 3 illustrates the features of this embodiment.

Figure 1B:
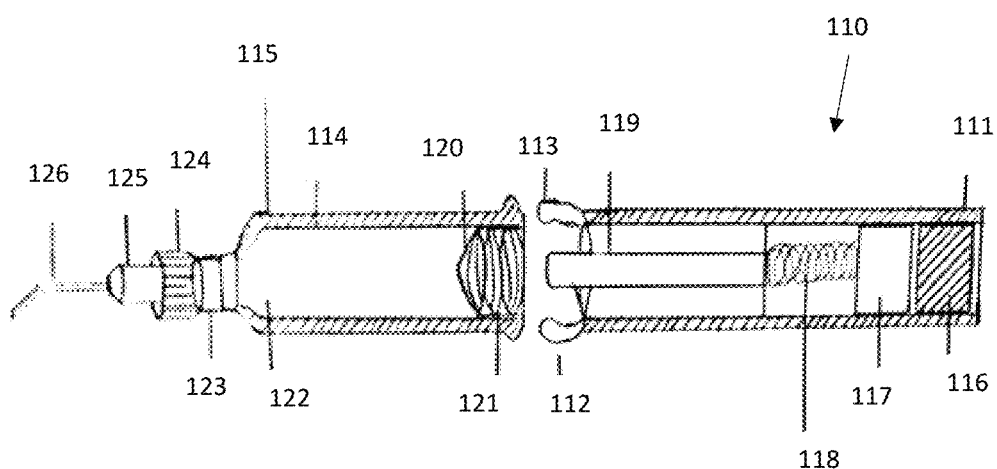

In some embodiments, the actuation assembly (110) within the housing has a proximal end and distal end. The distal end portion of the actuation assembly may have a coupler (112) with two hinges (113) that are disposed approximately equidistance circumferentially about the coupler (112), configured to engage the flange of the cartridge container (115) at two distinct circumferential locations where the coupler (112) is hinged to the cartridge container. In preferred embodiments, the actuation assembly is wrapped in a flexible sterile silicon wrap that protects from breaching the sterile barrier. The features of this embodiment are illustrated in FIG. 1b.

In further embodiments, the pen-injector of present invention further may comprise the housing encompassing end of the cartridge holder and the inner body of the actuation assembly.

In the present context, the actuation assembly comprises a battery (116) which may be provided as an alkaline, lithium, or any other type of battery, for single use or rechargeable in nature. It is also contemplated that the power source consists in a non-rechargeable battery of specific size and power specifically adapted for use in this device. This allows to realize a particularly simple solution of a cable-free operable device, with significantly less constraints both on the manufacturer's side, e.g. in terms of compliance with legal regulations in the medical sector concerning power sources and chargers, as well as on the user's side, e.g. in terms of keeping multiple pieces which otherwise would have to be furnished with the device, like a battery charger for rechargeable batteries.

The power source may consist of a single cell unit or of multiple cell units working in series or in parallel. Alternatively, the power source may also be provided as a capacitor or super capacitor capable of storing electrical energy. The injection device according to the present invention thus does not require any cables outside its casing, i.e. it is a cable-free electrically actuated device. The battery supplies electrical power for triggering the injection of medicament which drives the motor to apply an extrusion force or the spring itself compels the force to drive the rod or compressible spring causing the pushing of the plunger rod in the distal direction of the cartridge towards the needle.

As illustrated in FIG. 4, a novel drug delivery device (400) of the present invention comprises an over cap (401) covering the cartridge assembly which may be locked with actuation assembly, when not in use. The over cap is made of polypropylene and is designed in such a way so as to lock itself with the body of the housing containing the actuation assembly, such that it gives the appearance of a unitary whole when in locked position. During operation, the over cap may be removed and a needle assembly is attached for dispensing the medicament. After use, the over cap may be replaced in its position.

The cartridge assembly comprises a cartridge holder (402) preferably made of polypropylene constructed for housing a cartridge (403) comprising the medicament to be delivered. The cartridge holder (402) has as opening at its distal end allowing for insertion of a needle assembly and a circumferential flange at its proximal end, facilitating the locking of the cartridge with the actuation assembly, closed at the proximal end by a piston (410) made of polypropylene. In preferred embodiments, the cartridge is a multiple dose glass cartridge.

In preferred embodiments, the cartridge holder and a pre-sterile cartridge constitute a separate isolated unit, which may be easily attached during operation or detached when not in use. The isolated unit is so designed as to facilitate easy and firm locking of the said unit with the device at the time of dispensing the medication. The isolated unit may be sterilized and fixed to the device so that the medicament may be used during surgery or post-surgery as and when required.

Further, the device is designed to accommodate an actuation assembly comprising a rechargeable/replaceable battery (404), electrically supported by and connected to a PCB (405), followed by a motor (406) providing the driving force for dispensing the medicament comprising of electronic command circuit through the cartridge aided by a plunger rod (411) passing from the motor towards the piston. The actuation assembly is also provided with buttons (407) on the PCB for delivering accurate doses of the medicament.

In some embodiments, the actuation assembly at the proximal end is covered by housing covers on both the sides (e.g. dorsal cover (408) and ventral cover (409)), made of a thermoplastic polymer, namely ABS (acrylonitrile butadiene styrene) which account for the resistance, toughness and shiny impervious surface of the body of the housing.

In some embodiments, the battery is mechanically and electronically supported by one or more printed circuit boards (PCBs). A PCB generally consists of a copper sheet laminated on a non-conductive substrate, etched with conductive pathways or tracks to connect electronic components.

Figure 4A:
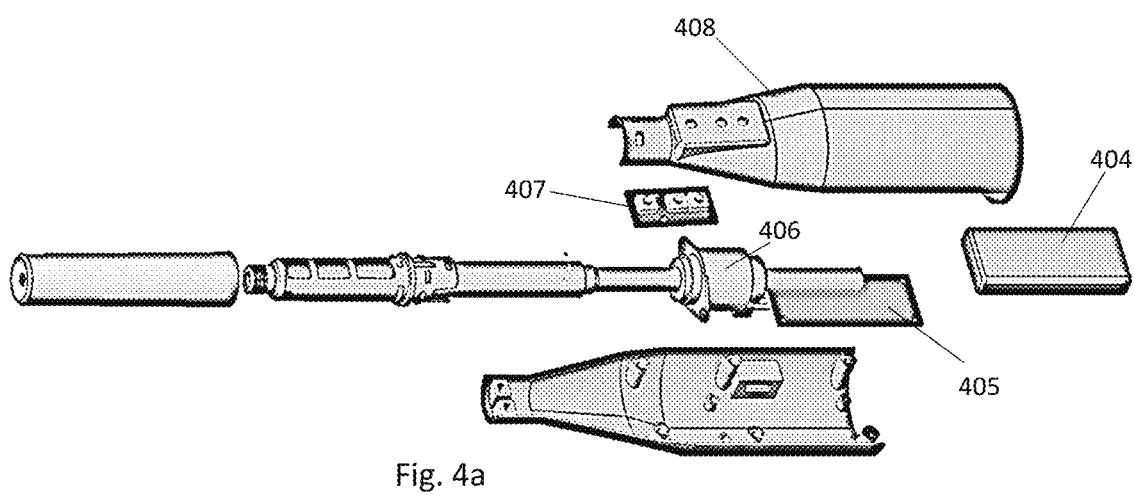
FIG. 4a illustrates the exploded view of the device with emphasis on the dorsal view of the top housing cover.

FIG. 4a shows an exploded view of the novel ophthalmic device of the present invention illustrating the alignment and arrangement of actuation assembly comprising a power source in the form of a battery (404), electronically supported by a PCB (405), followed by a motor providing the driving force for delivery of the medicament through the cartridge by means of plunger rod (411) extending from the motor (406) through the piston at the rearward opening of the cartridge. The PCB is provided with buttons (407) on it for delivering desired dosage of medicament. FIG. 4a also illustrates a dorsal view of the housing cover (408) of the device with provision for engaging the buttons PCB board with the housing cover of the device.

Figure 4B:
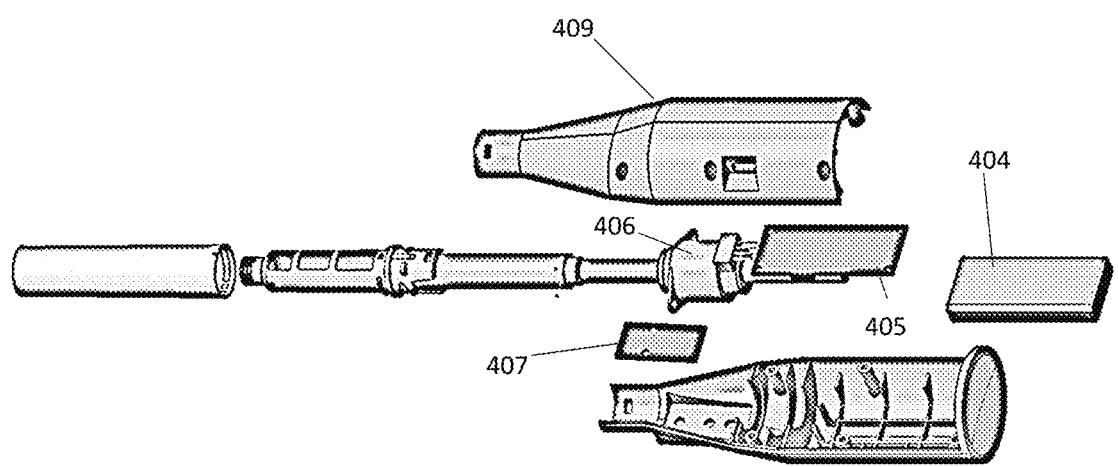
FIG. 4b illustrates the exploded view of the device with emphasis on the ventral view of the top housing cover.

FIG. 4b also represents an exploded view of the ophthalmic delivery device of the present invention with emphasis on the ventral view of the top cover (409) of the housing of actuation assembly.

Figure 5A:
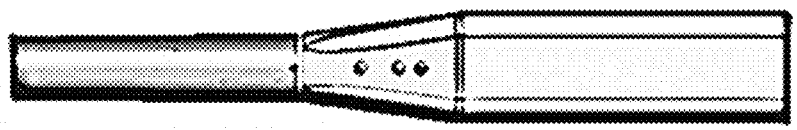
FIGS. 5a & 5b illustrates the front and side views of the novel drug delivery device.
Figure 5B:
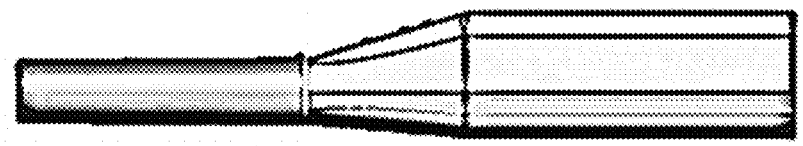

FIGS. 5a and 5b are representative of the front and side views of an entire assembly of the pen-injector according to one embodiment of the present invention.

Figure 6:
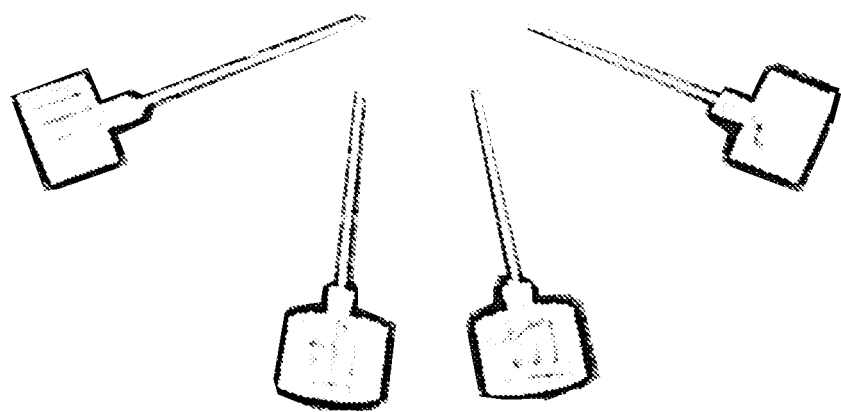
FIG. 6 shows the needles which may be affixed to the device during operation.

FIG. 6 represents the needles for dispensing the medicament during use. The needles comprise a cylindrical body made of polypropylene and a stainless steel syringe for passing the medicament there through. The needles are so designed to facilitate easy locking with the cartridge during use.

In another embodiment, the present invention provides a novel, intracameral device in the form of a pen injector which is electronically controlled, or cable-free motor driven, or combinations thereof, so constructed to be handheld, mobile, easily chargeable, flexible to operate with or without a cable. Preferably, the intracameral pen injector of the present invention may be carried for surgical camps.

In another embodiment of present invention discloses exposure to harmful microorganisms can be prevented by utilizing the correct sterilization methods. Though they are invisible to the naked eye, organisms capable of causing infection are everywhere. Sterile bandages, instruments, and equipment are necessary for preventing infection.

The use of steam under pressure is most commonly used to sterilize items. The three factors that dictate the success of steam sterilization are temperature, pressure and exposure time. Increasing pressure of steam in a closed container causes the temperature of the steam to rise. When microbes are exposed to the correct temperature and pressure for the right amount of time, they are destroyed and the items they were on become sterile. The device used for steam sterilization is called an autoclave. The minimum time, temperature, and pressure required to sterilize items is 10 minutes at 275° F. or 15 minutes at 250° F. and 15 pounds per square inch of pressure.

Exposure of microorganisms to saturated steam under pressure in an autoclave achieves their destruction by the irreversible denaturation of enzymes and structural proteins. The temperature at which denaturation occurs varies inversely with the amount of water present. Sterilization in saturated steam thus requires precise control of time, temperature, and pressure. As displacement of the air by steam is unlikely to be readily achieved, the air should be evacuated from the autoclave before admission of steam. This method should be used whenever possible for aqueous preparations and for surgical dressings and medical devices.

The recommendations for sterilization in an autoclave are 15 minutes at 121-124° C. (200 kPa). The temperature should be used to control and monitor the process; the pressure is mainly used to obtain the required steam temperature. Alternative conditions, with different combinations of time and temperature, are given below.

TABLE 1

| Different Conditions of Time and Temperature | | |
|---|---|---|
| Temperature (° C.) | Approximate Corresponding Pressure (KPa) | Minimum Sterilization Time (Min) |
| 126-129 | 250 | 10 |
| 134-138 | 300 | 5 |

Minimum sterilization time should be measured from the moment when all the materials to be sterilized have reached the required temperature throughout. Monitoring the physical conditions within the autoclave during sterilization is essential. To provide the required information, temperature-monitoring probes should be inserted into representative containers, with additional probes placed in the load at the potentially coolest parts of the loaded chamber (as established in the course of the validation programme). The conditions should be within ±2° C. and ±10 kPa (±0.1 atm) of the required values. Each cycle should be recorded on a time-temperature chart or by other suitable means.

Autoclaves use pressurized steam to destroy microorganisms, and are the most dependable systems available for the decontamination of laboratory waste and the sterilization of laboratory glassware, media, and reagents and devices. For efficient heat transfer, steam must flush the air out of the autoclave chamber. Autoclaves should be tested periodically with biological indicators like spores of *Bacillus stearothermophilus* to ensure proper function. This method of sterilization works well for many metal and glass items but is not acceptable for rubber, plastics, and equipment that would be damaged by high temperatures.

Another embodiment of the present invention discloses the use of Gas Sterilization in place of moist heat sterilization.

The chemically reactive gases such as formaldehyde, (methanol, H.CHO) and ethylene oxide (CH2)2O possess biocidal activity. Ethylene oxide is a colourless, odourless, and flammable gas.

The mechanism of antimicrobial action of the two gases is assumed to be through alkylations of sulphydryl, amino, hydroxyl and carboxyl groups on proteins and amino groups of nucleic acids. The concentration ranges (weight of gas per unit chamber volume) are usually in range of 800-1200 mg/L for ethylene oxide and 15-100 mg/L for formaldehyde with operating temperatures of 45-63° C. and 70-75° C. respectively.

The sterilizing efficiency of ethylene oxide depends on the concentration of the gas, the humidity, the time of exposure, the temperature, and the nature of the load. In particular, it is necessary to ensure that the nature of the packaging is such that the gas exchange can take place. It is also important to maintain sufficient humidity during sterilization. Records of gas concentration and of temperature and humidity should be made for each cycle. Appropriate sterilization conditions must be determined experimentally for each type of load.

After sterilization, time should be allowed for the elimination of residual sterilizing agents and other volatile residues, which should be confirmed by specific tests. Ethylene oxide gas has been used widely to process heat-sensitive devices.

The present invention discloses a sterile cover preferably made of plastic, more preferably thermoplastic, most preferably Polyethylene. The said device is packed inside the plastic cover and sterilized by means of moist heat sterilization or gas sterilization depending upon the heat sensitivity of the medicament used.

Figure 7:
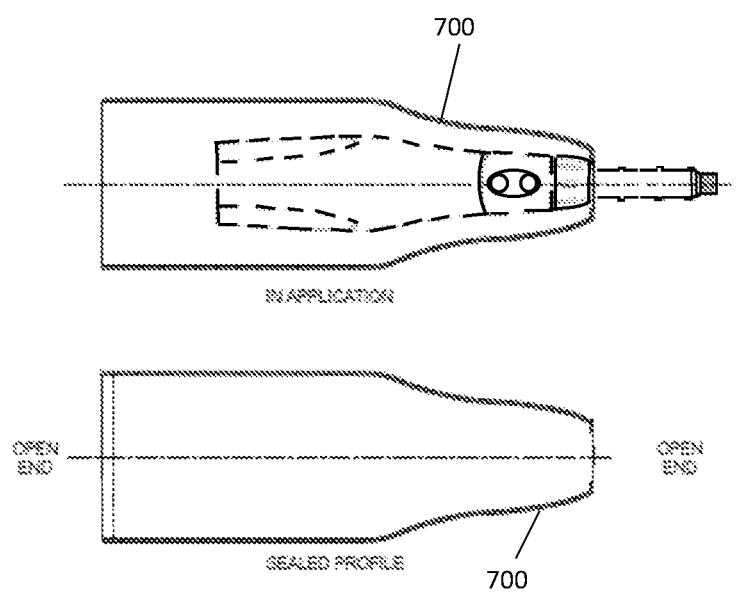
FIG. 7 shows an exemplary sterile protective plastic made cover for ophthalmic devices. It may look oversized, but once it expands in volume due to insertion of the device, it will properly fit.

The device depicted in FIG. 7 comprises a sterile, disposable protective cover (700) made from a soft optical material such as organic polymer, rubber etc., that is capable of conforming to the shape of the device. The protective cover comprises an elastic body that has a shape conforming to the shape of the inserted device. Initially it may look oversized. But once it expands in volume due to insertion of the device, it will be properly fit.

The material of construction of the protective cover is plastic, more specifically thermoplastic, most specifically Polyethylene. The polyethylene arrives at the plastic bag manufacturing facility in pellet form, referred to as resin. The machine used to create the plastic bags is an extruder and die assembly.

The manufacturing procedure of the plastic cover has been described below.

1. The machine operator pours the polyethylene resin into the hopper.
2. The hopper feeds the resin into the extruder.
3. Heating elements and the turning of the extruder screw melts the resin into molten form and forces it through the extruder.
4. The molten poly flows evenly up and over the circular die.
5. As the molten poly emerges from the die, the machine operator:
   a. Grabs it wearing protective gloves.
   b. Pinches the molten poly together.
   c. Ties a rope to the top of the molten poly. The rope leads upward to a pulley system.
   d. Pulls the other end of the rope to move the molten poly upwards. At the same time, the air ring blows cool air upwards, which solidifies the molten poly.
6. As the tubular shape moves up, the machine operator inserts an air gun through the poly film to blow in additional air. This step is repeated until the diameter of the tubular poly film reaches the required bag size.
7. Along the length of the tower are guides to keep the tubular poly film from shifting. As the film reaches the top of the cooling tower, the guides gradually flatten it into a lay flat form.
8. At the top of the cooling tower, motorized nip rollers grab the solidified poly film. The nip rollers now take over the job of moving the poly film up the cooling tower.
9. The lay-flat film travels over a series of rollers. For simple bags, such as trash bags or industrial bags, the film is contained to a single, in-line process. In this case, the polyethylene film:
   Travels through a bag machine that seals the bottom of the plastic bag and perforates it at the same time. The perforation allows the bags to be easily torn from the roll.
   May also travel through a separator that breaks the perforations and stacks the poly bags on top of each other for bulk packaging in a box.
10. For poly bags with Ziploc closure, the film is wound on a roll and then taken out of line for further processing at a converting facility. A converting facility has a variety of specialized equipment to create the Ziploc features.

The Finished plastic cover is wrapped around the ophthalmic device. The protective cover has a shape conforming to the shape of the inserted device. The user has to rip off the cover and it can be used readily without even sterilizing further.

The final packaging is sterilized using moist-heat sterilization or gas sterilization depending on the heat or moist sensitivity of the therapeutic agent prefilled.

Another embodiment of the present invention discloses a novel ophthalmic drug delivery device for intracameral delivery of therapeutic agents in the form a pen-injector for the treatment of ocular diseases and conditions in subject in need thereof.

Figure 8:
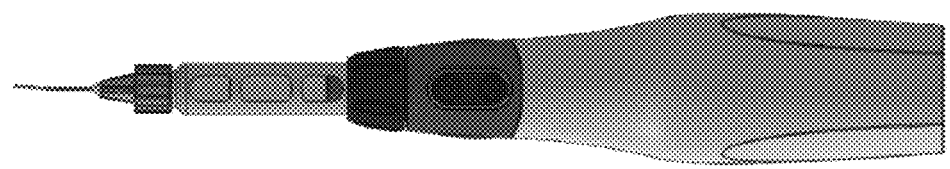
FIG. 8 represents a complete exemplary view of invention device in different perspectives having a 'chop stick' grip.
Figure 8:
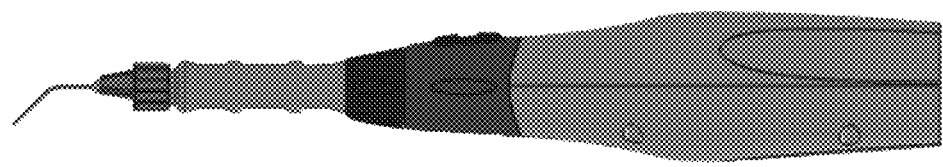

FIG. 8 represents a complete exemplary view of an embodiment from top and side perspectives exemplifying the "Chopstick like grip".

Figure 9A:
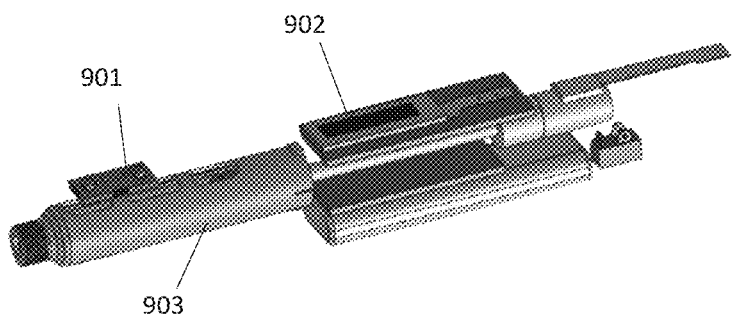
FIG. 9(a-c) depicts the exploded view of the device focusing on (i) Multimode power on/off button and (ii) OLED screen.
Figure 9B:
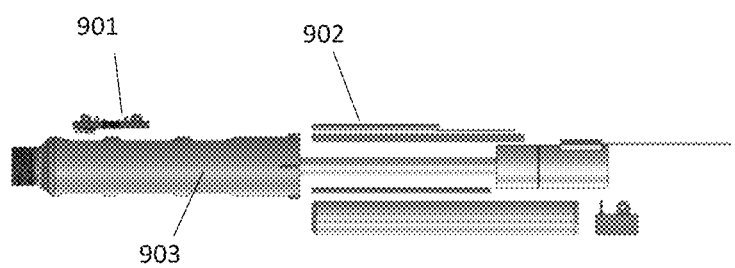
Figure 9C:
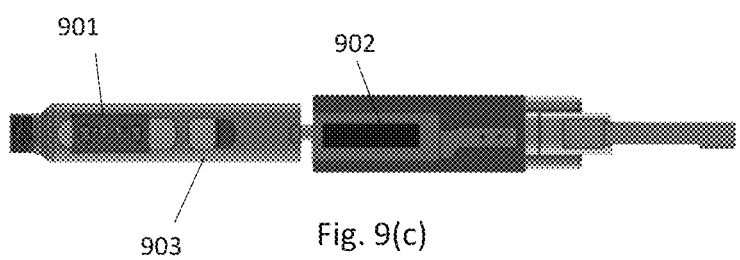

FIG. 9(*a-c*) depicts the exploded view of a device focusing on (i) Multimode power on/off button (901) and (ii) OLED screen (902). In another embodiment, the device comprises a cartridge container (903) disposed within the housing. The cartridge container has a generally elongated, hollow body sized to receive within the housing. The elongated hollow body has a hollow interior sized to receive the cartridge therein. The hollow body has an opening such that a pre-sterile cartridge can be located in the hollow interior and to permit the plunger rod to be slidably received within the cartridge. The cartridge container is designed so as to accommodate various sized cartridges. The cartridge housing may be made of moldable materials such as metal or plastic to ensure sterility, particularly during surgery. In some embodiments, the cartridge housing may be modified so as to incorporate other surgical modules like optical fibers; surgical cautery's. The multimode power on/off button (901) stationed near to tip thus providing the device with a "pen-like grip", would also work with a "pulse mode" to deliver a fixed quantity of product and also double up as a speed control to stimulate the rate of injection, and the OLED Screen (902) provides feedback of the quantity of medicament injected. The OLED screen might be used as a visual indicator to the quantity of medicament injected and the quantity of medicament left within the cartridge.

As FIG. 9(*a-c*) demonstrate the "Pen like grip" of the device differentiates the present invention from devices already known to enable the user to better grasp the device which is required specifically when administering the therapeutic agent on the face. The inventors of present invention have changed the grip of the device from an earlier "Chopstick" (FIG. 8) kind of a grip to a "Pen grip" (FIG. 9(*a-c*)) by moving the button controls forward to the tip of the cartridge where the needle is attached thus imparting greater control to the user and improving the usage of the product greatly. Moreover, this unique feature of the present invention can extend the usage of the said device even with the dermal filler.

The Multi mode On/Off power button might contain three switches having different functionality (i) Power button is to start (On) or stop (Off) the operation, (ii) Long button implies the Forward mode and (iii) short button to work with a "pulse mode" to deliver a fixed quantity of product and also double up as a speed control, high speed or low speed as per requirement, to stimulate the rate of injection.

For all control modes of the device, the electronic command circuit of the motor system may be programmed such as to allow control of the device by a On and Off button which activates, and respectively stops, the motor of the motor system, by an On button followed by release of said button to activate, respectively stop the motor by one of these modes at the user's choice according to his personal preferences.

According to the present invention, the intracameral drug delivery device is configured for the prevention or treatment of diseases or conditions, including without limitation, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

According to present invention, the intracameral for ophthalmic delivery may carry balanced salt solution as supplement and also not limited to a solution containing solution of electrolytes as supplement as well.

According the present invention, the Intracameral for ophthalmic delivery may carry various actives for administration into eye selected from those of antibiotics, steroids, monoclonal antibodies, hyaluronic acid compounds or derivatives thereof and may also be useful to carry hydroxyl propyl methyl cellulose or derivatives or related compounds as inactive. The term antibiotic is not limited to antibacterials, are a type of antimicrobial used in the treatment and prevention of bacterial infection.

They may either kill or inhibit the growth of bacteria. Antibiotics may also possess antiprotozoal activity. Antibiotics are not effective against viruses such as the common cold or influenza Erythromycin, Clindamycin, Gentamycin, Tetracycline, Meclocycline, and (Sodium) sulfacetamide or combinations thereof. Most of the eye infections are treated with combination of antibiotics and steroids. Thus term antibiotic is also related to combination of steroid and antibiotics. The type of combination is chosen based on the type of eye infection all about. The combinations may be selected from dexamethasone, tobramycin, loteprednol, sulfacetamide sodium, neomycin, polymyxin B, prednisolone, bacitracin, hydrocortisone, fluromethololone, gentamicin or combinations thereof.

The term 'HA' is not limited to Hyaluronic Acid (HA) or its derivatives or combinations thereof, HA is also known as hyaluronan or hyaluronate, is a carbohydrate, more specifically a mucopolysaccharide occurring naturally throughout the human body. It can be several thousands of sugars (carbohydrates) long. When not bound to other molecules, it binds to water giving it a stiff viscous material. This viscous Gel is one of the most heavily researched substances; the inventors of the present application have attempted to deliver the same using the device in eye surgery. Its function in the body is, amongst other things, to bind water and to lubricate movable parts of the body, such as eye muscles.

The term MAB (mono clonal antibody) is not limited to the following otherwise selected from wherein the monoclonal antibody is selected from the group consisting of abagovomab, afelimomab, anatumomabmafenatox, arcitumomab, bectumomab, besilesomab, capromab, edobacomab, edrecolomab, elsilimomab, enlimomab, enlimomabpegol, epitumomabcituxetan, ibritumomabtiuxetan, imciromab, inolimomab, mitumomab, oregovmab, satumomab, sulesomab, technetium (99mTc) nofetumomabmerpentan, tositurnomab, vepalimomab, zolimomabaritox, adalimumab, adecatumumab, belimumab, bertilimumab, denosumab, efungumab, golimumab, ipilimumab, iratumumab, lerdelimumab, lexatumumab, mapatumumab, metelimumab, ofatumumab, panitumumab, pritumumab, raxibacumab, sevirumab, stamulumab, ticilimumab, tuvirumab, votumumab, zalutumumab, zanolimumab, abciximab, basiliximab, bavituximab, cetuximab, ecromeximab, galiximab, infliximab, keliximab, lumiliximab, pagibaximab, priliximab, rituximab, teneliximab, volocix-imab, alemtuzumab, apolizumab, aselizumab, bapineuzumab, bevacizumab, bivatuzumab, cantuzumabmertansine, certolizumabpegol, daclizumab, eculizumab, efalizurnab, epratuzumab), fontolizumab, gemtuzumab, inotuzumabozogamicin, labetuzumab, lintuzumab, matuzumab, mepolizumab, motavizumab, natalizumab, nimotuzumab, ocrelizumab, omalizumab, palivizumab, pascolizumab, pertuzumab, pexelizumab, ranibizumab, reslizumab, rovelizumab, ruplizumab, sibrotuzumab, siplizumab, sontuzumab, tadocizumab, talizumab, tefibazumab, tocilizumab, toralizumab, trastuzumab, tucotuzumabcelmoleukin, urtoxazumab, visilizumab, yttrium (90Y)tacatuzumabtetraxetan, and IgG or combinations thereof.

The present invention involves the delivery of the mono clonal antibody delivery using the novel device, the term MAB is not limited to the following or otherwise selected from wherein the monoclonal antibody is selected from the group consisting of: abagovomab, afelimomab, anatumomabmafenatox, arcitumomab, bectumomab, besilesomab, capromab, edobacomab, edrecolomab, elsilimomab, enlimomab, enlimomabpegol, epitumomabcituxetan, ibritumomabtiuxetan, imciromab, inolimomab, mitumomab, oregovomab, satumomab, sulesomab, technetium (.sup.99mTc) nofetumomabmerpentan, tositumomab, vepalimomab, zolimomabaritox, adalimumab, adecatumumab, belimumab, bertilimumab, denosumab, efungumab, golimumab, ipilimumab, iratumumab, lerdelimumab, lexatumumab, mapatumumab, metelimumab, ofatumumab, panitumumab, pritumumab, raxibacumab, sevirumab, stamulumab, ticilimumab, tuvirumab, votumumab, zalutumumab, zanolimumab, abciximab, basiliximab, bavituximab, cetuximabaecromeximab, galiximab, infliximab, keliximab, lumiliximab, pagibaximab, priliximab, rituximab, teneliximab, volociximab, alemtuzumab, apolizumab, aselizumab, bapineuzumab, bevacizumab, bivatuzumab, cantuzumabmertansine, certolizumabpegol, daclizumab, eculizumab, efalizumab, epratuzumab), fontolizumab, gemtuzumab, inotuzumabozogamicin, labetuzumab, lintuzumab, matuzumab, mepolizumab, motavizumab, natalizumab, nimotuzumab, ocrelizumab, omalizumab, palivizumab, pascolizumab, pertuzumab, pexelizumab, ranibizumab, reslizumab, rovelizumab, ruplizumab, sibrotuzumab, siplizumab, sontuzumab, tadocizumab, talizumab, tefibazumab, tocilizumab, toralizumab, trastuzumab, tucotuzumabcelmoleukin, urtoxazumab, visilizumab, yttrium.sup.90Y tacatuzumabtetraxetan, IgG-1, IgG-2, IgG-3, and IgG-4 or combinations thereof.

The terms "Antibody" or "antibody peptide(s)" refer to an intact antibody, or a binding fragment thereof that competes with the intact antibody for specific binding. Binding fragments are produced by recombinant DNA techniques, or by enzymatic or chemical cleavage of intact antibodies. Binding fragments include Fab, Fab', F(ab')$_2$, Fv, and single-chain antibodies. An antibody other than a "bispecific" or "bifunctional" antibody is understood to have each of its binding sites identical. An antibody substantially inhibits adhesion of a receptor to a counterreceptor when an excess of antibody reduces the quantity of receptor bound to counterreceptor by at least about 20%, 40%, 60% or 80%, and more usually greater than about 85% (as measured in an in vitro competitive binding assay).

The present invention involves the delivery of the mono clonal antibody delivery using the novel device, the term 'polypeptide' is not limited to the following or otherwise selected from wherein the Examples of polypeptides include insulin like growth factor-I (IGF-I or Somatomedin-C), insulin, calcitonin, leptin, hGH, human parathyroid hormone (PTH) or active fragments thereof, such as but not limited to PTH 1-31, PTH 1-34 and PTH 3-34, melatonin, GLP-1 or Glucagon-like peptide-1, GiP, OB-3 peptide, pituitary adenylatecyclase neuropeptide-activating polypeptide, GM-1 ganglioside, nerve growth factor (NGF), D-tryp6)-LHRH, nafarelin, FGF, VEGF, VEGF antagonists, Leuprolide, interferon-alpha, interferon-beta, interferon-gamma, low molecular weight heparin, PYY, LHRH, LH, GDNF, G-CSF, Ghrelin antagonists, Ghrelin, KGF, Integrelin, Nesiritide, cetrorelix acetate, ganirelix acetate, bivalirudin, zafirlukast, Exanitide, pramlintide acetate, vasopressin, desmopressin, glucagon, ACTH, GHRH and analogs, oxytocin, corticotropin releasing hormone, TRHrh, atrial natriuretic peptide, thyroxine releasing hormone, FSH, prolactin, Tobramycin, Triptorelin, Goserelin, Buserelin, Octreotide, Gonadorelin, Felypressin, Deslorelin, Vasopressin, 8-L-Arg, Eptifibatide, GM-CSF, EPO, Interleukin-11, Endostatin, Angiostatin, N-acetyl oxyntomodulin 30-37, Oxyntomodulin, Ularitide, Xerecept, Apo A-IV, rNAPc2, Secretin, Thymopentin, Neuromedin U, Neurotensin, Thrombospondin-1 inhibitors, FGF-18, FGF-20, FGF-21, Elcatonin Acetate, Antide Acetate, Dynorphin A (1-13) Acetate, Sincalide, Thymopentin Acetate, Thymosin alphal acetate (Thymalfasin), Fertirelin Acetate, CRF Acetate, CRF (ovine), Hisrelin, Thymalfasin, Ecallantide, Oxycortin, Urocortin, Spiegelmer nucleotide aptamers, CGRP (calcitonin gene related protein), Urocortin, Amylin, IL-21, melanotan, valpreotide, ACV-1 neuropathic pain peptide, gastrin, gastrin releasing peptide (GRP), gastrin releasing peptide-like peptides, or epidermal growth factor or combinations thereof.

The term HPMC (Hydroxyl propyl methyl cellulose) is not limited to an average molecular weight between about 10,000 and 13 million. Preferred cellulosic polymers include: hydroxypropyl methyl cellulose (HPMC), hydroxyethyl cellulose (HEC), hydroxypropyl cellulose (HPC) and methyl cellulose (MC). In general, these cellulosic polymers are present in the compositions of the present invention at a concentration between about 0.05 and about 5.0 percent by weight (wt %), preferably between about 0.25 and about 1.0 wt %. It is especially preferred to use the cellulosic polymers at a concentration of about 0.5 wt %.

The invention having been disclosed in connection with the foregoing embodiments, additional variations will now be apparent to persons skilled in the art. Various modifications and variations to the above described pen-injector can be made without departing from the scope of the invention.

From the foregoing it will be understood that the embodiments of the present invention described above are well suited to provide the advantages set forth, and since many possible embodiments may be made of the various features of this invention and as the device herein described may be varied in various parts, all without departing from the scope of the invention, it is to be understood that all matter hereinbefore set forth or shown in the accompanying drawings is to be interpreted as illustrative and that in certain instances some of the features may be used without a corresponding use of other features, all without departing from the scope of the invention.

Further the present invention has been illustrated in the different figures. The following specific and non-limiting steps for functioning need to be construed as merely illustrative, and do not limit the present disclosure in any way whatsoever.

We claim:

1. A cable-free, motor driven ophthalmic device for delivering a dose of a medicament, the device further comprising:

(a) a sterile cartridge assembly at a distal end of the device, the cartridge assembly containing the medicament and having a proximal end and a distal end;

(b) an actuation assembly at a proximal end of the device covered with a housing coupled to the proximal end of the cartridge assembly, the housing comprising top and bottom housing covers, and the actuation assembly comprising a motor, a battery, and a plunger rod all positioned proximal of the cartridge assembly;

(c) a removable over cap covering the cartridge assembly and removably locked to the housing of the actuation assembly;

(d) the motor connected to an electronic command circuit;

(e) a multimode button assembly coupled to the electronic command circuit to control dose and speed of the medicament delivered from the device, the multimode button assembly located along a distal portion of the cartridge assembly toward the cartridge assembly distal end;

(f) an OLED Screen to function as a visual indicator for the dose delivery, the OLED Screen located proximal relative to the cartridge assembly and multimode button assembly;

(g) a sterile protective cover having open ends at opposite sides of the cover, the cover disposed over at least the housing and conforming to the shape of the housing; and (h) wherein the multimode button assembly comprises at least a first button and a pulse mode button and wherein the pulse mode button delivers a fixed amount of the medicament and also acts as a speed control.

2. The device of claim 1, wherein the cartridge assembly comprises a cartridge holder with a pre-sterile multiple dose glass cartridge having a rearward opening therein and containing the medicament, the cartridge assembly confined at the proximal end by a piston slidably received within the rearward opening of the cartridge, the multimode button assembly located proximate the cartridge holder and toward the distal end of the device.

3. The device of claim 2, wherein the cartridge assembly constitutes a separate removable unit that may be sterilized prior to coupling to the housing assembly.

4. The device of claim 2, wherein the actuation assembly comprises a printed circuit board (PCB) connected to the multimode button assembly and a replaceable battery electronically supported by the PCB, the PCB operatively connected to the plunger to control displacement and speed of the plunger.

5. The device of claim 4, wherein the battery provides energy for driving the motor and thereby the piston within the cartridge assembly for dispensing the medicament by means of the plunger rod, the plunger rod extending from the motor towards the piston of the cartridge within the housing of the device.

6. The device of claim 1, further comprising a needle assembly couplable to the housing of the actuation assembly when the over cap is removed.

7. The device of claim 1, wherein the sterile protective cover is made of plastic, polyethylene, resin, rubber, polystyrene, polypropylene, polycarbonate, nylon, or a combination thereof.

8. The device of claim 1, wherein the removable over cap covering the cartridge assembly and removably locked to the housing of the actuation assembly has an outer dimension similar to an outer dimension of the housing of the actuation assembly.

9. The device of claim 1, wherein the multimode button assembly further comprises a power button and a forward mode button.

10. The device of claim 9, wherein the multimode button assembly further comprises one or more buttons for dosage adjustment.

11. The device of claim 1, wherein the sterile protective cover is made of polyethylene.

12. The device of claim 1, further comprising a cartridge container for receiving a cartridge, the cartridge container having a front end with a hold for receiving a needle and a rear end having a flange for engaging the actuation assembly within the housing.

13. The device of claim 12, wherein the actuation assembly comprises a coupler with at least two hinges configured to engage the flange of the cartridge container at two distinct circumferential locations.

14. The device of claim 12, wherein the cartridge container comprises polypropylene.

15. The device of claim 1, wherein the top and bottom housing covers comprise a thermoplastic polymer.

16. The device of claim 15, wherein the top and bottom housing covers comprise acrylonitrile butadiene styrene.

* * * * *